United States Patent [19]

Dittmar et al.

[11] Patent Number: 4,528,991
[45] Date of Patent: Jul. 16, 1985

[54] MICROWAVE APPLICATOR FOR CREATING LOCAL HYPERTHERMIAS

[75] Inventors: André Dittmar, Lyons; Georges Delhomme, Bron; Jean-Pierre Pellissier, Villeurbanne; Michel Schmitt, Lyons, all of France

[73] Assignee: Centre National de la Recherche Scientifique (CNRS), Paris, France

[21] Appl. No.: 393,710

[22] Filed: Jun. 30, 1982

[30] Foreign Application Priority Data

Jul. 1, 1981 [FR] France ................................ 81 13075

[51] Int. Cl.³ ............................................... A61N 5/02
[52] U.S. Cl. ............................ 128/804; 219/10.55 R; 219/10.55 F
[58] Field of Search ................. 128/804; 219/10.55 R, 219/10.55 F

[56] References Cited

U.S. PATENT DOCUMENTS

| 2,567,757 | 9/1951 | Argento | 128/804 |
| 4,140,130 | 2/1979 | Storm | 128/804 |
| 4,240,445 | 12/1980 | Iskander et al. | 128/804 |
| 4,341,227 | 7/1982 | Turner | 128/804 |

FOREIGN PATENT DOCUMENTS

| 868324 | 1/1953 | Fed. Rep. of Germany . |
| 2068970 | 9/1971 | France . |
| 2178049 | 11/1973 | France . |
| WO80/0014-62 | 7/1980 | PCT Int'l Appl. . |

OTHER PUBLICATIONS

Bahl et al., "A New Microstrip Radiator . . . ", IEEE Trans. On Microwave Theory & Techniques, vol. 28, No. 12, Dec. 1980, pp. 1464-1465.
Brezovich et al., "A Practical System . . . Hyperthermia", Int. J. Rad. Oncology Biol. Phys., vol. 7, pp. 423-430, Mar. 1981.

Primary Examiner—Lee S. Cohen
Attorney, Agent, or Firm—Stevens, Davis, Miller Mosher

[57] ABSTRACT

An applicator of microwaves, has a first mass connected to a wave guide and associated with a heat exchanger in connection with a circuit for circulation of a cooling fluid on the one hand, and a second mass in the form of an envelope concentric with respect to the first mass connected to the return of the wave guide and having an annular base associated with a heat exchanger in connection with a circuit for circulation of a cooling fluid. The invention is particularly directed to the treatment of cancerous tumours.

12 Claims, 8 Drawing Figures

MICROWAVE APPLICATOR FOR CREATING LOCAL HYPERTHERMIAS

FIELD OF THE INVENTION

The present invention relates to devices used for creating, within a determined mass and by means of micro-waves, zones of localized hyperthermia.

The invention relates mainly to applicators of the above type used in experiments in the treatment of cancerous tumours.

BACKGROUND OF THE INVENTION

In the above technical field experiments have been carried out for several years in an attempt to treat cancerous tumours. These experiments have demonstated that the specific action of hyperthermia results in regression of the cancerous tumours. These experiments have also shown that hyperthermia increases the sensitivity of the cells to various chemical substances and thus enables use of chemo-therapy in the treatment of cancerous tumours. In addition, hyperthermia apparently also increases the effect of the ionizing radiations on the cancerous cells.

Microwaves may therefore be used, a priori, as therapeutic agents, because they may penetrate deeply into the biological tissue and thus reach remote tumours.

However, heretofore conducted experiments have disclosed a basic problem which is an incontestable obstacle to the development of such experiments on the biological tissue.

In fact, it has been observed that, due to their proximity to the applicator, surface tissues absorb more energy than deep tissues at whose level the hyperthermia must generally be directed to treat a tumour. To obtain a sufficient rise in temperature, of the order of 42° to 44° C. for example in deep tissues, it has been observed that the surface tissues and the skin in particular, underwent too great a rise in temperature, leading to degradation thereof and, moreover, imposing on the patients an intolerable physical stress with the durations of exposure generally employed.

Such a method and applicator for carrying it out cannot be developed until this problem has been solved so that it becomes possible to effect a deep local hyperthermia without inflicting a considerable rise in temperature intolerable for the surface tissues.

It is precisely an object of the present invention to find a solution to this problem by proposing a new type of applicator which enables the temperature of the surface tissues to be regulated whilst ensuring a deep hyperthermia.

It is an object of the invention to propose a new applicator which is of reliable design and easily produced at a particularly advantageous cost price.

It is another object of the invention to provide a new applicator which does not have dimensions substantially greater than means known at present, whilst making it possible to regulate as desired the temperature of the surface tissues.

A further object of the invention is to use means for attaining the purposes mentioned above which are capable of performing a second function of monitoring position, form in the general sense and dimensions of the local zones subjected to hyperthermia.

SUMMARY OF THE INVENTION

To attain the above purposes, the apparatus according to the invention is characterised in that, in an applicator of the type comprising two metal masses of high heat conductivity, of different polarities, disposed without direct physical contact near each other and of which one is associated with a guide wave for microwaves produced by a generator, one of the masses is connected to the wave guide and, near its surface of application, is provided with a heat exhanger in connection with a circuit for circulation of a cooling fluid, and the other mass is in the form of an envelope concentric with respect to said first mentioned mass, connected to the return of the wave guide, surrounding the first mass without touching it and forming at least one annular base having a surface of application located substantially in the plane of that of the first mass, said surface being associated with at least one heat exchanger in connection with a circuit for circulation of a cooling fluid.

BRIEF DESCRIPTION OF THE DRAWINGS

The invention will be more readily understood on reading the following description with reference to the accompanying drawings, in which.

DETAILED DESCRIPTION OF THE INVENTION

Figure 1:
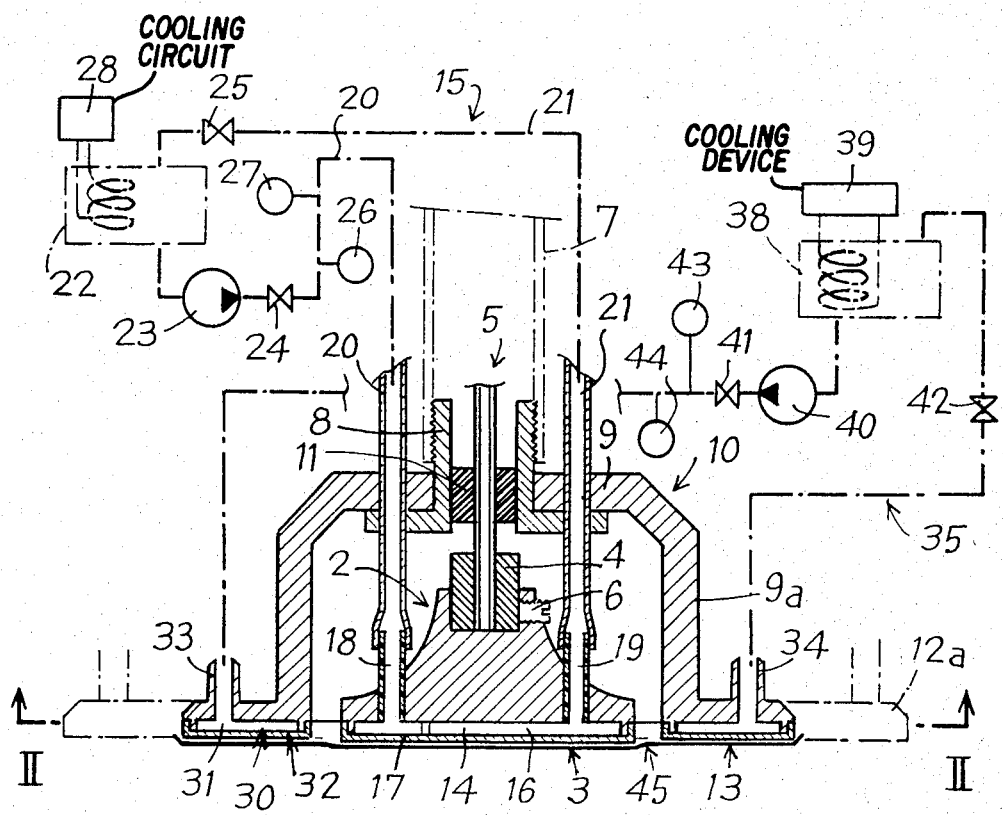
FIG. 1 is an elevation in section of the applicator according to the invention.
Figure 2:
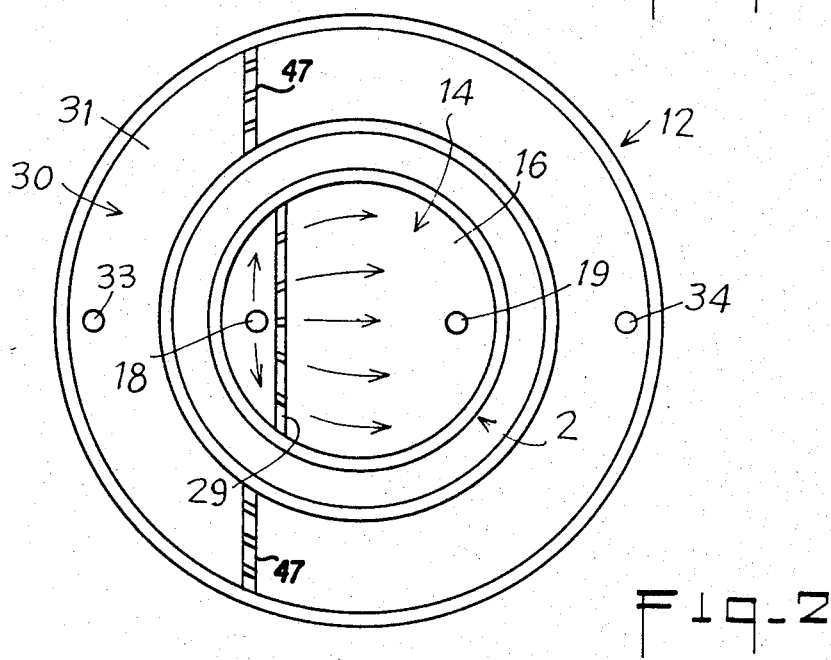
FIG. 2 is a view from underneath taken along line II—II of FIG. 1.

Referring now to the drawings, according to the embodiment illustrated in FIGS. 1 and 2, the microwave applicator, generally designated by reference numeral 1, comprises, with a view to creating localized hyperthermias, a first mass 2 of high heat conductivity, preferably made of an alloy of light metals, such as Duraluminium. Opposite a surface 3 for application on the tissue to be treated, mass 2 is provided with a ring 4 made of conducting material for connection with a wave guide 5, for example constituted by a coaxial conductor. The connection between ring 4 and mass 2 may be rendered adjustable via a set screw 6. The coaxial conductor 5 is provided with a so-called return sheath 7 which is fixed and centred on a bushing 8 made of conducting material, passing through the top 9 of a second mass 10 made of a material of high heat conductivity, for example identical to the material constituting mass 2. The connection between return sheath 7, bushing 8 and mass 10 is utilized to ensure centering of coaxial conductor 5 via a centering sleeve II made of insulating material.

Second mass 10 is in the form of a bell comprising, from the top 9, an envelope 9a, for example circular, which extends coaxially to the mass 2 without having any physical contact therewith. At its lower edge, the envelope 9a forms an annular base 12 having a surface of application 13 extending substantially in the same plane as surface 3. The mass 10 may be made in one or more parts.

Mass 2 is associated with a heat exchanger 14 which is in connection with a circuit 15 for circulation of a cooling fluid. The heat exchanger 14 is preferably formed by a recess 16 made in the mass 2 from the surface of application 3 over a constant small depth. The recess 16 presents in plan, as apparent in FIG. 2, the form of a cylindrical cavity. The recess 16 is closed by a removable plate or cover 17, made of a material of high heat conductivity and which may be fitted, screwed, welded or joined in any other appropriate manner so as to establish tightness of the closure of the recess 16 constituting the heat exchanger 14. The outer surface of the cover 17 then represents the face of application 3.

Mass 2 also comprises at least two connecting tubes 18 and 19 which may be constituted by tubular segments, for example made of plastics material, incorporated in the mass 2 and opening inside the recess 16. The tubes 18 and 19 ensure connection with two pipes 20 and 21 forming part of circuit 15. Pipes 20-21 are maintained at mass 10 level by passing through the bottom of the envelope 9a. Pipes 20 and 21 represent, respectively, a return circuit and an intake circuit for a cooling fluid, particularly water, taken from a buffer tank 22 by a pump 23. In addition to valves 24 and 25, the circuit 15 comprises a flow meter 26 and a thermometer 27. The tank 22 may be associated with a cooling circuit generally designated by reference 28.

FIG. 2 shows that the tubes 18 and 19 preferably open out diametrically opposite each other in the exchanger 14. An internal disturbing means 29 may possibly be provided to promote a distributed flow and better circulation of the cooling fluid inside the exchanger 14, and thus increase the exchange capacities of the exchanger by avoiding any zone of lesser circulation or any dead zone.

Annular base 12 of the second mass 10 is also associated with a heat exchanger 30, preferably formed by a recess 31 made from the face 13. The recess 31 is defined over a constant depth, in the manner of an annular chamber or cavity. The recess 31 is closed by a cover 32 made of a material of high conductivity, which may be removably fitted or rendered fast with the base 12 by screwing, gluing, welding or any other appropriate means, to established a tight closure. The outer face of the annular cover 32 then represents the surface of application 13.

Heat exchanger 30 is connected, via tubes 33 and 34 formed by or incorporated in the annular base 12, with a circuit 35 for circulation of a cooling fluid such as water. The circuit 35 comprises two pipes 36 and 37 respectively representing return and intake circuits, with respect to a buffer tank 38 possibly associated with a cooling device 39. The circuit 35 also comprises a circulation pump 40, two valves 41 and 42 and a flow meter 43 and thermometer 44.

According to another arrangement of the invention, the concentric disposition of masses 2 and 10 is ensured by a foil or film 45 made of insulating material added by adhesion to cover, without interruption, the outer faces of the covers 17 and 32 located substantially on the same plane.

One or more circulation disturbing means 47 may also be disposed inside the exchanger 30, as for exchanger 14.

The functioning of the applicator may be described simply as far as the path of the microwaves is concered. In fact, the coaxial conductor 5 ensures the advance of the microwaves furnished by the generator, for example a magnetron, up to the level of mass 2 inside which they are distributed to follow, by the periphery, the cover 17 allowing looping and return via the annular cover 32, the base 12 and the mass 10, itself connected to the return sheath 7.

Figure 3:
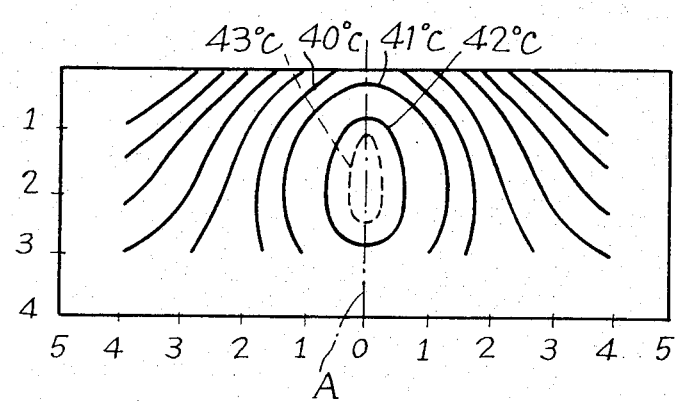
FIG. 3 is a diagram showing temperature curves which may be obtained in a tissue with an applicator of conventional type.

The application of such an applicator on a tissue, for example biological tissue, then allows a rise in temperature or localized hyperthermia to be created, of the type illustrated schematically in FIG. 3, insofar as the following conditions are for example combined:

ambient temperature: 20° C.
power applied to the generator of microwaves: 15 watts
frequency range employed: 2 450 MHz In this diagram, it is observed that a locally induced hyperthermia, of the order of 43° C., is created in a zone of between 1 and 3 cm depth with respect to the surface of application with a radial radiation of the order of 0.5 cm with respect to the centre of the applicator designated by axis A. It is also ascertained, by the different isotherms, that the mere application, as stated above, leads to subjecting the surface tissues to a rise in temperature of up to about 40° C.

Such an applicator can therefore not be validly employed in view of the risk of physical stress and deterioration, particularly burns, inflicted on the superficial layers of the tissue treated.

Figure 4:
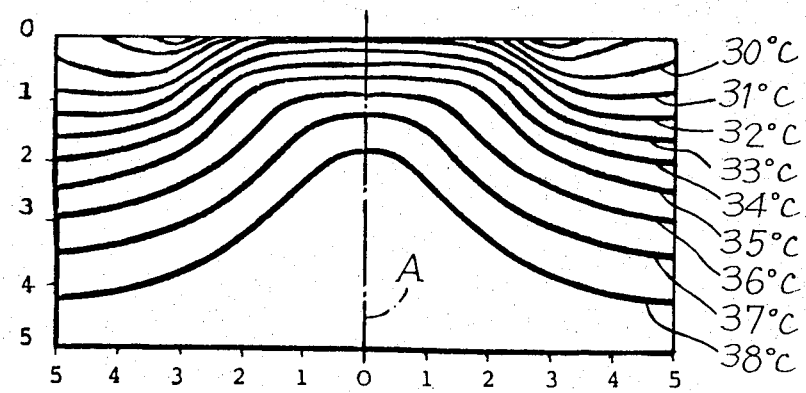
FIGS. 4 to 7 are diagrams similar to that of FIG. 3, but demonstrating the possibilities of variants of the object of the invention.

FIG. 4 shows the use of the same device described hereinabove, but this time employing the means provided according to the invention to effect localized superficial cooling of the zone to be treated. In such an example, the following parameters are employed:

microwave power: 10 watts
frequency employed: 2 450 MHz
temperature of the cooling fluids: 20° C.
rate of flow circuit 15: 10 ml/mn
rate of flow circuit 35: 10 ml/mn An examination of FIG. 4 will show that these conditions lead to an induced hyperthermia whose form, dimensions, localization and depth are notably different from those of FIG. 3. In fact, a temperature substantially equal to 30° C. at a depth of between 2.5 and 4 cm is noted in a zone between 0.5 and 2 cm of radial radiation from axis A. This Figure also shows that the surface temperature is substantially of the order of 13° C., hence a temperature rise considerably less than that of the localized hyperthermia in depth.

Figure 5:
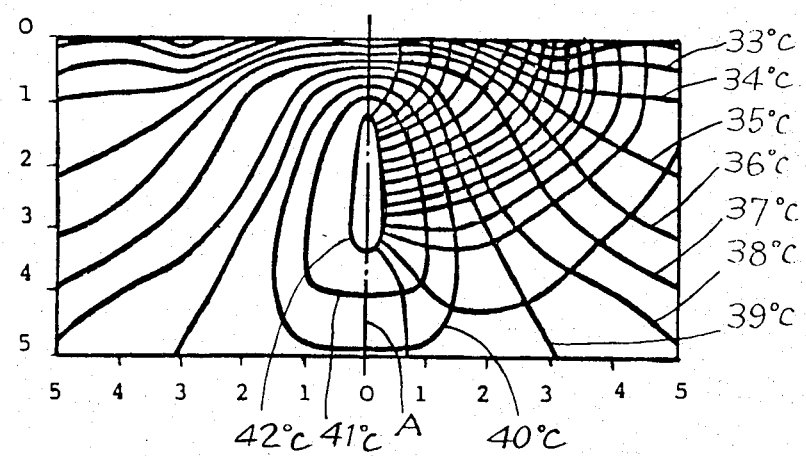

FIG. 5 shows an example of hyperthermia corresponding to the use of the applicator with a view to treating a cancerous cell.

In this example, the following conditions are combined:

micro wave power: 20 watts
frequency employed: 2 450 MHz
temperature of the cooling liquids: 20° C.
rate of flow circuit 15: 15 ml/mn rate of flow circuit 35: 20 ml/mn Examination of FIG. 5 shows the existence of a localized hyperthermia of temperature of the order of 42° C. in localization of the closed type, located at a depth of between 1 and 5 cm with respect to the superficial layers and radiating over about 1.5 cm from axis A. This Figure also shows that, under the above conditions, the superficial layer of tissue treated has a temperature of the order of 33° C.

Comparison of FIGS. 4 and 5 thus shows that the effect of the circulation of the cooling fluid in the exchangers 14 and 30 is to remove the calories resulting from the absorption of the superficial layers and, consequently, to maintain the latter at an appropriate and acceptable optimal temperature, whilst creating in depth the desired hyperthermia. Depending on the conditions of use of the applicator, i.e. the power and frequency employed, it therefore becomes possible, by modifying the parameters of circulation of circuits 15 and 35, to ensure acceptable temperatures in the superficial layers which are independent of the deep hyperthermia.

A comparison of FIGS. 4 and 5 also shows that annular base 12 performs a second function, in addition to that of cooling. In fact, by modifying the conditions of circulation for circuit 35, it becomes possible to model the form of the induced hyperthermia, for example by increasing the function of cooling to bring the low-value isotherms down on the axial part of the induced hyperthermia. Consequently, the annular base 12 performs a function of heat focusing means, limiting the lateral propagations of the deep hyperthermias and thus allowing the creation of a zone of hyperthermia, for example having a form elongated in height according to the example of FIG. 5. It thus becomes possible, by modifying the parameters accordingly, to choose the conformation in closed or open zone of the induced hyperthermia to make it correspond, in volume, as closely as possible to that of the cell to be treated.

FIG. 5 also shows the lines of thermal flux resulting from the removal of calories by the heat exchangers.

Figure 6:
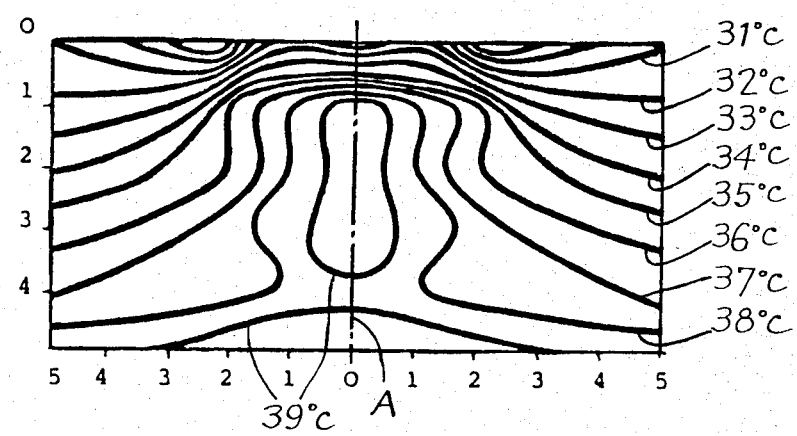

FIG. 6 shows a different example of conformation of an induced hyperthermia employing the following conditions of application:

micro wave power: 20 watts
frequency: 2 450 MHz
temperature of the cooling fluids: 20° C.
rate of flow of circuit 15: 30 ml/mn
rate of flow of circuit 35: 20 ml/mn With such conditions, a surface temperature of the order of 32° C. is attained, whilst a localized hyperthermia of the order of 39° C. is established over a depth of 1 to 4 cm and over about 1 cm of radiation from axis A.

Figure 7:
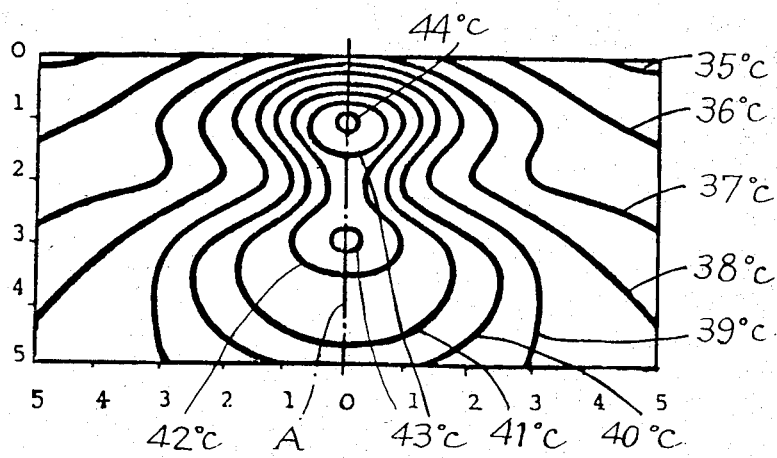

FIG. 7 shows a different result obtained with the following conditions:

microwave power: 75 watts
frequency: 2 450 MHz
temperature of the cooling fluid: 20° C.
rate of flow of circuit 15: 25 ml/mn
rate of flow of circuit 35: 50 ml/mn With conditions such as those mentioned hereinabove, a surface temperature of 38° C. has been obtained with creation of a hyperthermia in closed zone but with double focus, with a temperature of the order of 44° C. at about 1 cm depth over about 1 cm radiation from axis A and a temperature of 43° C. established at about 3 cm depth with a radiation of the order of 1 cm from axis A.

This means according to the invention consequently make it possible substantially to reduce the surface temperature of the tissue on which the applicator is applied, whilst establishing a desired hyperthermia in the deep layers and, additionally, to give this hyperthermia an overall zone or virtual volume of influence, of open or closed conformation, with single or double focus, which may consequently be adapted substantially to the localization and conformation of an identified tumour to be treated.

As stated hereinabove, the coaxial arrangement of the masses 2 and 10 which may be qualified respectively as central conductor and cooler and as peripheral conductor and cooler, is established via the foil or film 45. This film is preferably chosen to be of plastics material of small thickness, of the order of 0.1 mm. This results in a high heat conductivity in the axial sense, in view of the small thickness and large relative surface. Therefore, the film 45 does not brake the heat exchanges between the applicator and the tissues to be treated. On the other hand, heat conductivity of the film in the radial sense is very low, with the result that heat exchanges between the central cooler and the heat focusing means are reduced to a minimum. It should be noted that the film 45 performs the additional function of electrical protection of the tissue, as it covers all the metal parts of high conductivity which may be brought into contact with the biological tissue to be treated.

It is important to emphasize that the construction of the object of the invention makes it possible to effect a complete looping at each heat exchanger 14 or 30, via the mass and the plate 17 or 32 of conducting material. Consequently, the micro waves find a natural conducting circuit and may close around the cavities 16 and 31 in which the sheets of cooling fluid circulate, without this resulting in the latter heating up.

The central part is shown in the form of a compact mass, but it must be considered that, with a view to reducing thermic inertia, it is possible to provide an embodiment wherein, for example, a central recess is employed which allows only one path for the microwaves.

For an applicator employing the parameters as furnished hereinabove, the recess 16 or 31 may be given a depth of 0.7 mm making it possible to obtain mean linear speeds of circulation greater than 20 mm/s for a rate of flow of cooling of 0.5 cm$^3$/s. Such a mean linear speed is favourable to heat exchanges and gives a rapid response. Likewise to this end, the plates 17 and 32 may be provided to have a thickness of the order of 0.3 mm.

Figure 8:
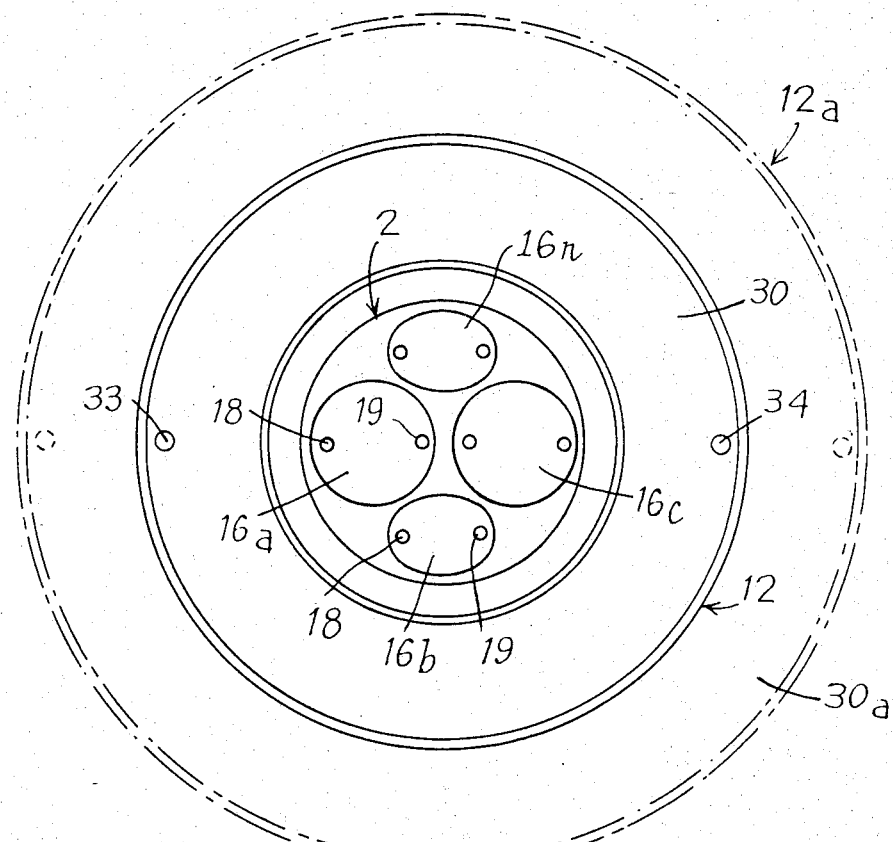
FIG. 8 is a view from underneath, similar to FIG. 2, illustrating a possible variant of one of the elements constituting the object of the invention.

FIG. 8 shows that the exchanger 14 may comprise a plurality of recesses, 16a–16n, provided with either a common cover or individual closing covers, each being supplied via its own tube from the circulation circuit 15.

FIGS. 1 and 8 show, in dashed and dotted lines, that the mass 10 may be provided with an annular base 12a adapted to support two exchangers 30 and 30a side by side, independent of each other.

The present invention is not limited to the embodiments described and shown, as various modifications may be made thereto without departing from its scope. In particular, provision may be made for the fluids for cooling the two masses to circulate in opposite directions.

What is claimed is:

1. A microwave applicator for creating local hyperthermias, said applicator being of the type comprising first and second metallic masses having high heat conductivity and different polarities and being disposed without direct physical contact with each other, said first mass being associated with a wave guide for microwaves produced by a microwave generator, comprising:
   (a) a microwave wave guide;
   (b) a cooling fluid circulation circuit;
   (c) a first metallic mass electrically connected to said microwave wave guide and having a first application surface, a first heat exchanger being disposed adjacent said first application surface, said first heat exchanger being associated with said cooling fluid circulation circuit; and
   (d) a second metallic mass including an envelope portion disposed substantially concentrically with respect to said first metallic mass and electrically connected to a return associated with said wave guide, said envelope portion surrounding said first metallic mass without physical contact therewith and including an annular base having a second application surface, said second application surface being substantially coplanar with said first application surface, a second heat exchanger being disposed adjacent said second application surface, said second heat exchanger being associated with said cooling fluid circulation circuit.

2. The applicator as recited in claim 1, wherein said first heat exchanger includes a recess formed in said first metallic mass and connected to said cooling fluid circulation circuit by at least two connection elements, and said second heat exchanger includes a recess formed in said second metallic mass and connected to said cooling fluid circulation circuit by at least two connection elements.

3. The applicator as recited in claim 2, wherein said first and second heat exchangers are substantially concentric and coplanar.

4. The applicator as recited in claim 1 or 2, wherein said circulation circuit comprises first and second circulation circuits having first and second regulating means to regulate fluid flow through said first and second circulation circuits respectively, said first and second heat exchangers being connected to different ones of said first and second circuits.

5. The applicator as recited in claim 4, wherein said first heat exchanger includes a recess having circulation disturbing means for providing distributed flow and increased cooling fluid circulation inside said first heat exchanger.

6. The applicator as recited in claim 4, wherein said second heat exchanger includes a recess having circulation disturbing means for providing distributed flow and increased cooling fluid circulation inside said second heat exchanger.

7. The applicator as recited in claim 2, wherein said first heat exchanger includes a recess formed in said first metallic mass in said first application surface, said recess having a substantially constant depth and being closed by a cover which comprises a conductive plate.

8. The applicator as recited in claim 2, wherein said second heat exchanger includes a recess formed in said second metallic mass in said second application surface, said recess having a substantially constant depth and being closed by a cover which comprises a conductive plate.

9. The applicator as recited in claim 1, wherein said second metallic mass is bell-shaped and includes means for supporting said wave guide, for supporting connection elements for connecting said first heat exchanger with said cooling fluid circulation circuit, and for supporting said first metallic mass.

10. The applicator as recited in claim 1, wherein said first and second application surfaces are connected by a foil of insulating material.

11. The applicator as recited in claim 1, wherein said first and second application surfaces are connected by a film of insulating material.

12. The applicator as recited in claim 1, wherein said first metallic mass includes a central recess.

* * * * *